(12) United States Patent
Toso et al.

(10) Patent No.: US 11,932,589 B2
(45) Date of Patent: Mar. 19, 2024

(54) HYDROFLUOROOLEFINS AND METHODS OF USING SAME

(71) Applicant: 3M INNOVATIVE PROPERTIES COMPANY, St. Paul, MN (US)

(72) Inventors: Nicholas A. Toso, Minneapolis, MN (US); Michael J. Bulinski, Stillwater, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 204 days.

(21) Appl. No.: 17/431,590

(22) PCT Filed: Feb. 12, 2020

(86) PCT No.: PCT/IB2020/051153
§ 371 (c)(1),
(2) Date: Aug. 17, 2021

(87) PCT Pub. No.: WO2020/170080
PCT Pub. Date: Aug. 27, 2020

(65) Prior Publication Data
US 2022/0135503 A1    May 5, 2022

Related U.S. Application Data

(60) Provisional application No. 62/807,273, filed on Feb. 19, 2019.

(51) Int. Cl.
| | | |
|---|---|---|
| *C07C 21/18* | (2006.01) | |
| *C07C 23/08* | (2006.01) | |
| *C07C 23/10* | (2006.01) | |
| *C09K 5/04* | (2006.01) | |
| *C11D 1/722* | (2006.01) | |
| *C11D 3/24* | (2006.01) | |
| *C11D 3/43* | (2006.01) | |

(52) U.S. Cl.
CPC .............. *C07C 21/18* (2013.01); *C07C 23/08* (2013.01); *C07C 23/10* (2013.01); *C09K 5/045* (2013.01); *C11D 3/245* (2013.01); *C11D 1/722* (2013.01); *C11D 3/43* (2013.01)

(58) Field of Classification Search
CPC ......... C07C 21/18; C07C 23/08; C07C 23/10; C09K 5/045
See application file for complete search history.

(56) References Cited

U.S. PATENT DOCUMENTS

| | | | |
|---|---|---|---|
| 9,653,762 | B2 | 5/2017 | Shimura et al. |
| 2006/0106263 | A1 | 5/2006 | Miller et al. |
| 2012/0011864 | A1 | 1/2012 | Leck et al. |
| 2016/0009974 | A1 | 1/2016 | Benanti et. al. |
| 2018/0141893 | A1 | 5/2018 | Lamanna et al. |

FOREIGN PATENT DOCUMENTS

| | | |
|---|---|---|
| EP | 2684870 | 1/2014 |
| RU | 2003124319 | 2/2005 |
| WO | 2018/057134 | 3/2018 |

OTHER PUBLICATIONS

JP 45028977 abstract, Muramatsu et al., ethylene having perfluoro unsaturated four-member ring (1965).*
LaZerte, J. D. et al, Journal of the American Chemical Society, vol. 77, pp. 910-914, Feb. 20, 1955, The Free Radical Catalyzed Addition of Alcohols and Aldehydes to Perfluoroolefins.
Ellis, "Cleaning and Contamination of Electronics Components and Assemblies", Electrochemical Publications, 1986, pp. 182-195.
Furin, "Partly Fluorinated Alcohols as Semi-Products for Synthesis of Fluoroorganic Compounds", Fluorine Notes, 2007, vol. 01, No. 50, pp. 1-2.
International Search Report for PCT International Application No. PCT/IB2020/051153, dated Jul. 31, 2020, 4 pages.

* cited by examiner

*Primary Examiner* — Jafar F Parsa
(74) *Attorney, Agent, or Firm* — Jeffrey M. Olofson

(57) ABSTRACT

A hydrofluoroolefin compound is represented by the following general formula (I): where $R_F1$ is a hydrogen atom or $CH_3$, and (iii) $R_F1$ is a linear or branched perfluorinated alkyl group having 1 to 10 carbon atoms and optionally including one or more catenated heteroatoms; and $R_F2$ is a fluorine atom or a linear or branched perfluorinated alkyl group having 1 to 8 carbon atoms and optionally including one or more catenated heteroatoms; with the proviso that when RF2 is a fluorine atom, then RF1 includes at least 2 carbon atoms; or (iv) $R_F1$ and $R_F2$ are bonded together to form a ring structure having 4 to 8 carbon atoms and optionally including one or more catenated heteroatoms.

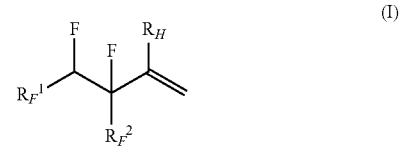

(I)

18 Claims, No Drawings

HYDROFLUOROOLEFINS AND METHODS OF USING SAME

CROSS REFERENCE TO RELATED APPLICATIONS

This application is a national stage filing under 35 U.S.C. 371 of PCT/IB2020/051153, filed Feb. 12, 2020, which claims the benefit of U.S. Provisional Application No. 62/807,273, filed Feb. 19, 2019, the disclosure of which is incorporated by reference in its/their entirety herein.

FIELD

The present disclosure relates to hydrofluoroolefins and methods of making and using the same, and to working fluids that include the same.

BACKGROUND

Various hydrofluoroolefin compounds are described in, for example, U.S. Pat. App. Pub. 2006/0106263 and RU Pat. Pub. 2245319.

SUMMARY

In some embodiments, a hydrofluoroolefin is provided. The hydrofluoroolefin is represented by the following general formula (I):

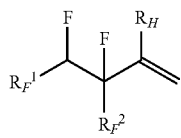

(I)

where $R_H$ is a hydrogen atom or $CH_3$; and
  (i) $R_F1$ is a linear or branched perfluorinated alkyl group having 1 to 10 carbon atoms and optionally including one or more catenated heteroatoms; and $R_F2$ is a fluorine atom or a linear or branched perfluorinated alkyl group having 1 to 8 carbon atoms and optionally including one or more catenated heteroatoms; with the proviso that when $R_F2$ is a fluorine atom, then $R_F1$ includes at least 2 carbon atoms; or
  (ii) $R_F1$ and $R_F2$ are bonded together to form a ring structure having 4 to 8 carbon atoms and optionally including one or more catenated heteroatoms.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

The ever-increasing demand for reliability, continuing miniaturization, and the growing number of faults in electronic components manufactured in no-clean processes all combine to put increased focus on the use of cleaning solvents in electronics manufacturing. There has been rapid growth in the electronics industry because of the swiftly rising demand for industrial as well as consumer electronics products. Cleaning solvents are specially engineered to dependably dissolve common manufacturing greases and oils (e.g., hydrocarbons having the formula $C_nH_{2n}+2$) used in the production of such industrial and consumer electronics products. Fluorinated cleaning solvents which demonstrate high levels of hydrocarbon solubility are suitable for such applications, in part, due to their low flammability, high density, low viscosity, low surface tension, and higher vapor pressure resulting in quick evaporation from components after use. Furthermore, in sharp contrast to hydrocarbon solvents, fluorinated cleaning solvents minimize the amount of residue left on components after cleaning.

Currently, fluids used for dissolving and removing such greases and oils (i.e., long chain hydrocarbons), or other organics from surfaces contain fluid blends that include, for example, trans-1,2-dichloroethylene, 1,1,1-trichloroethane (TCA), trichloroethylene, and dichloromethane. Regarding such fluid blends, one drawback to this approach is the tendency for a change in the composition ratio over the lifetime of the cleaning fluid. This change in composition ratio, in turn, leads to safety concerns and compromises the performance of the cleaning fluid. Therefore, a single composition cleaning fluid which is nontoxic, nonflammable, and high in hydrocarbon solubility would be of significant benefit to the electronics cleaning industry. Moreover, some of the materials currently employed are regulated by the Montreal Protocol as ozone depleting substances or have toxicity concerns.

In view of an increasing demand for environmentally friendly and low toxicity chemical compounds, in addition to strong cleaning ability, there exists a need for new long chain hydrocarbon alkanes cleaning fluids that provide low environmental impact and toxicity. Finally, such cleaning fluids should be capable of being manufactured using cost-effective methods.

Generally, the present disclosure provides a new class of compounds useful as cleaning fluids (or as components of cleaning fluids). The compounds are hydrofluoroolefins (HFOs), which provide better cleaning and physical properties to existing cleaning fluids, as well as provide lower atmospheric lifetimes, lower global warming potentials, and lower toxicities to provide a more acceptable environmental profile. Furthermore, the hydrofluoroolefins of the present disclosure can be manufactured cost-effectively.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "halogenated" (for example, in reference to a compound or molecule, such as in the case of "halogenated HFO") means that there is at least one carbon-bonded halogen atom.

As used herein, "fluoro-" (for example, in reference to a group or moiety, such as in the case of "fluoroalkylene" or "fluoroalkyl" or "fluorocarbon") or "fluorinated" means (i) partially fluorinated such that there is at least one carbon-bonded hydrogen atom, or (ii) perfluorinated.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to a hydrofluoroolefin represented by the following structural formula (I):

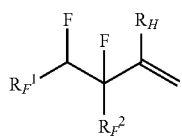

(I)

where $R_H$ is a hydrogen atom or $CH_3$; and
(i) $R_F1$ is a linear or branched perfluorinated alkyl group containing 1 to 10, 1 to 8, 1 to 6, or 1 to 4 carbon atoms and optionally including one or more catenated heteroatoms; and $R_F2$ is a fluorine atom (F) or a linear or branched perfluorinated alkyl group containing 1 to 8, 1 to 6, or 1 to 4 carbon atoms and optionally including one or more catenated heteroatoms; or
(ii) $R_F1$ and $R_F2$ are bonded together to form a ring structure having 4 to 8 or 4 to 6 carbon atoms and optionally including one or more catenated heteroatoms.

In some embodiments, when $R_F2$ is F, $R_F1$ includes at least 2 carbon atoms. In some embodiments, when $R_F2$ is F, and $R_F1$ includes 2 carbons, and $R_H$ is not $CH_3$.

In some embodiments, any of the above discussed catenated heteroatoms may be secondary O heteroatoms wherein the O is bonded to two carbon atoms. In some embodiments, any of the above discussed catenated heteroatoms may be tertiary N heteroatoms wherein the N is bonded to three perfluorinated carbon atoms.

In some embodiments, the hydrofluoroolefins of the present disclosure may possess excellent hydrocarbon solubility, rendering them highly suitable for use as cleaning solvents. In this regard, in some embodiments, any of the above described hydrofluoroolefins may have a solubility factor defined as follows:

Solubility Factor (SF)=((LSH/14)−1)−3.5 ((T−70)/70)²+0.643, where LSH is determined in accordance with the Largest Soluble Hydrocarbon Test of the Examples of the present disclosure and T is the normal boiling point of the fluid (in degrees Celsius). In some embodiments, LSH (at room temperature) may vary from 14 to 25, 17 to 23, or 17 to 21, in whole number increments. In some embodiments, any of the above described compounds may have a solubility factor (SF) of greater than 0, greater than 0.1, greater than 0.2, greater than 0.5, greater than 1.0, greater than 1.1, or greater than 1.2.

In some embodiments, the fluorine content in the hydrofluoroolefin compounds of the present disclosure may be sufficient to make the compounds non-flammable according to ASTM D-3278-96 e-1 test method ("Flash Point of Liquids by Small Scale Closed Cup Apparatus").

In various embodiments, representative examples of the compounds of general formula (I) include the following:

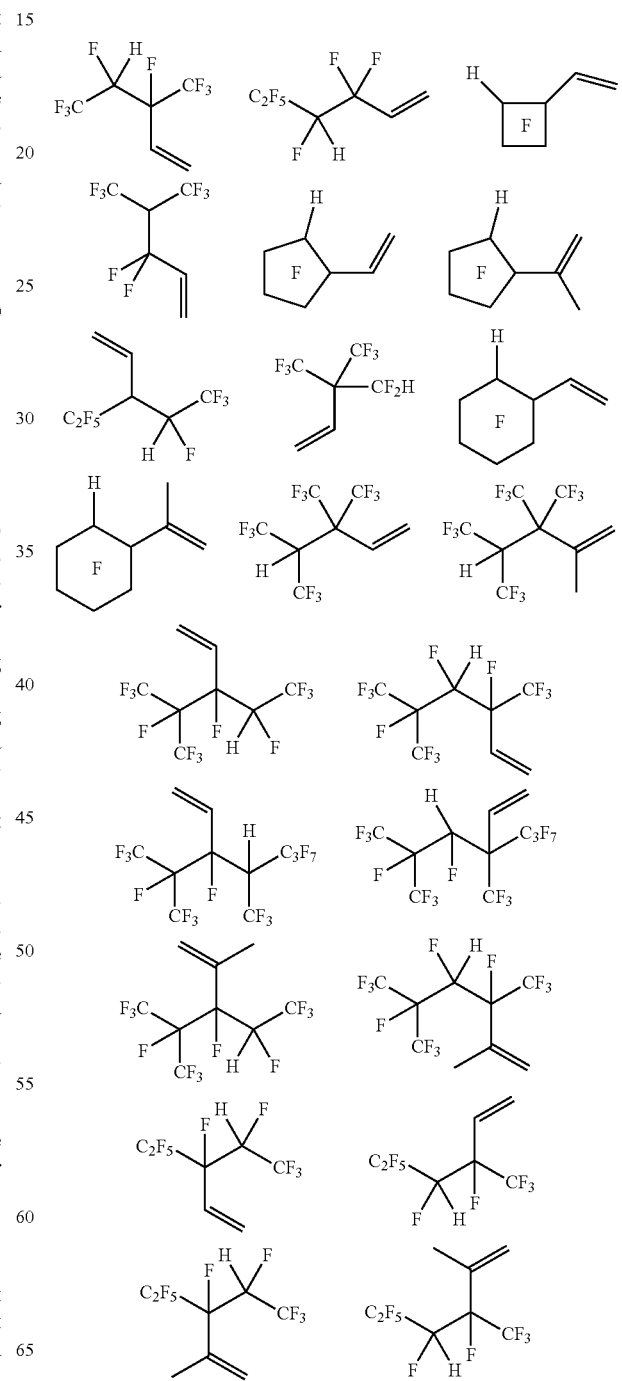

-continued

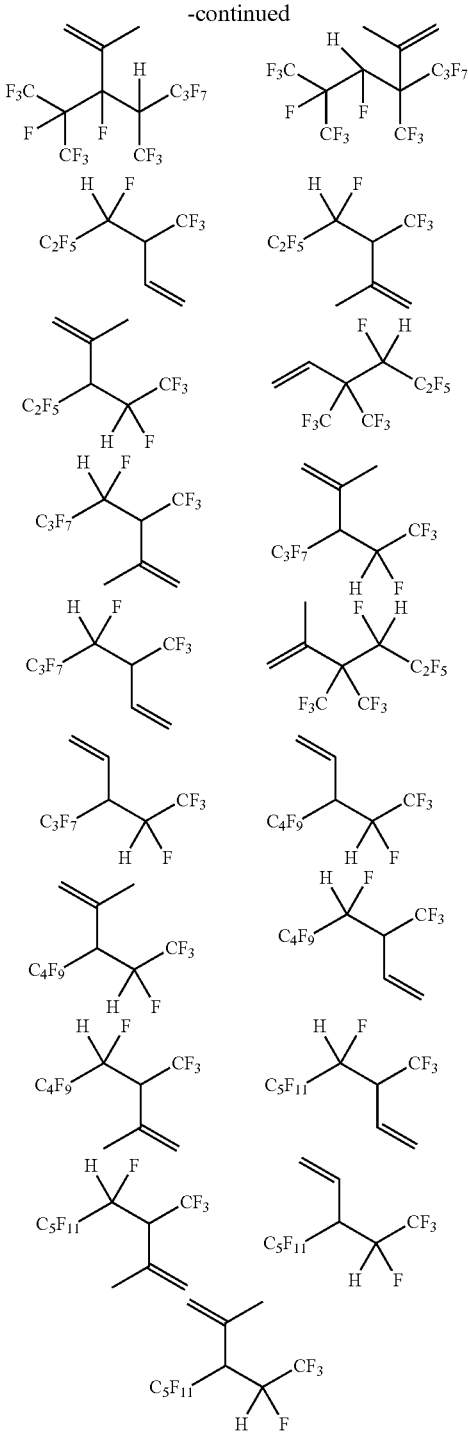

In some embodiments, the hydrofluoroolefins of the present disclosure may be useful over a broad operating temperature range. In this regard, in some embodiments, the hydrofluoroolefins of the present disclosure may have a boiling point of no lower than 30, 40 or 50 degrees Celsius and no higher than 130, 120, 110, 100, 90, or 80 degrees Celsius.

In some embodiments, the hydrofluoroolefins of the present disclosure may be hydrophobic, relatively chemically unreactive, and thermally stable. The hydrofluoroolefin compounds may have a low environmental impact. In this regard, the hydrofluoroolefin compounds of the present disclosure may have a global warming potential (GWP) of less than 500, 300, 200, 100, 10 or less than 1. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] dt}{\int_0^{ITH} a_{CO_2} [C_{CO_2}(t)] dt} = \frac{\int_0^{ITH} a_i C_{oi} e^{-t/\tau i} dt}{\int_0^{ITH} a_{CO_2} [C_{CO_2}(t)] dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, ti is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the compounds of the present disclosure may be produced by free radical addition of fluorinated olefins to hydrocarbon alcohols, followed by a two-step net dehydration via acetylation and pyrolysis of the acetate.

In some embodiments, the present disclosure is further directed to working fluids that include the above-described hydrofluoroolefin compounds as a major component. For example, the working fluids may include at least 25%, at least 50%, at least 70%, at least 80%, at least 90%, at least 95%, or at least 99% by weight of the above-described hydrofluoroolefin compounds, based on the total weight of the working fluid. In addition to the hydrofluoroolefin compounds, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrochloroolefins, hydrochlorofluoroolefins, hydrofluoroethers, sulfones, perfluorosulfones or mixtures thereof, based on the total weight of the working fluid. Such additional components can be chosen to modify or enhance the properties of a composition for a particular use.

In some embodiments, the present disclosure relates to cleaning compositions that include one or more hydrofluoroolefin compounds of the present disclosure. In use, the cleaning compositions may serve to remove (e.g., dissolve) contaminants from the surface of a substrate. In this regard, the present disclosure is further directed to compositions that include the hydrofluoroolefin compounds of the present disclosure and one or more contaminants (which have, for example, been removed from a substrate by the hydrofluoroolefin compounds). In such compositions, the hydrofluoroolefin compounds of the present disclosure may be present in an amount of at least 25 wt. %, at least 50 wt. %, at least 75 wt. %, at least 95 wt. %, or at least 99 wt. %, based on the total weight of the composition. In some embodiments, the contaminants may include long chain hydrocarbon alkanes (e.g., having the formula $C_nH_{2n}+2$, where n is greater than 5, 10, 15, or 20).

In some embodiments, the cleaning compositions of the present disclosure may include one or more co-solvents. In some embodiments, the hydrofluoroolefin compounds may be present in the cleaning compositions in an amount of greater than 50 weight percent, greater than 60 weight percent, greater than 70 weight percent, greater than 80 weight percent, greater than 90 weight percent, or greater than 95 weight percent, based upon the total weight of the hydrofluoroolefin compounds and the co-solvent(s).

In illustrative embodiments, the co-solvent may include alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. Representative examples of co-solvents which can be used in the cleaning compositions may include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene [remove from list?], cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclohexane, 3-methyl-1,1,2,2-tetrafluorocyclobutane, 1-hydropentadecafluoroheptane, or mixtures thereof. For example, such co-solvents can be chosen to modify or enhance the solvency properties of a cleaning composition for a particular use and can be utilized in ratios (of co-solvent to hydrofluoroolefin compounds) such that the resulting composition has no flash point.

In various embodiments, the cleaning compositions may include one or more surfactants. Suitable surfactants include those surfactants that are sufficiently soluble in the fluorinated olefin, and which promote contaminant removal by dissolving, dispersing, or displacing the contaminant. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily contaminant removal and another added to promote water-soluble contaminant removal. The surfactant, if used, can be added in an amount sufficient to promote contaminant removal. Typically, surfactant is added in amounts from 0.1 to 5.0 wt. %, or amounts from about 0.2 to 2.0 wt. %, based on the total weight of the surfactant(s) and the hydrofluoroolefin compounds.

In some embodiments, if desirable for a particular application, the cleaning compositions can further include one or more dissolved or dispersed gaseous, liquid, or solid additives (for example, carbon dioxide gas, stabilizers, antioxidants, or activated carbon).

In some embodiments, the present disclosure is further directed to the above-described cleaning compositions, in their post-clean state. In this regard, the present disclosure is directed to any of the above-described cleaning compositions that include one or more contaminants dissolved, dispersed, or otherwise contained therein.

In some embodiments, the contaminants may include light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed. In some embodiments, the hydrofluoroolefin compounds of the present disclosure may be particularly suited to remove long chain hydrocarbon alkane contaminants (e.g., hydrocarbons having the formula $C_nH_{2n}+2$, where n is greater than 9).

In some embodiments, the contaminants may be present in the post-clean cleaning composition (individually or collectively) in an amount of between 0.0001% and 0.1 wt. %, between 0.1 and 10 wt. %, or between 10 and 20 wt. %; or at least 5 wt. %, at least 10 wt. %, or at least 20 wt. %, based on the total weight of hydrofluoroolefins and contaminants in the post-clean composition.

In some embodiments, the cleaning compositions of the present disclosure can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986), which is herein incorporated by reference in its entirety.

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In some embodiments, the present disclosure relates to a process for cleaning a substrate. The cleaning process can be carried out by contacting a contaminated substrate with a cleaning composition as discussed above.

In some embodiments, the hydrofluoroolefin compounds of the present disclosure (or working or heat transfer fluids containing the same) can be used in various applications as heat transfer agents (for example, for the cooling or heating of integrated circuit tools in the semiconductor industry, including tools such as dry etchers, integrated circuit testers, photolithography exposure tools (steppers), ashers, chemical vapor deposition equipment, automated test equipment (probers), physical vapor deposition equipment (e.g. sputterers), and vapor phase soldering fluids, and thermal shock fluids).

In some embodiments, the present disclosure is further directed to an apparatus for heat transfer that includes a device and a mechanism for transferring heat to or from the device. The mechanism for transferring heat may include a heat transfer or working fluid that includes one or more hydrofluoroolefin compounds of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, heat exchangers, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility requires that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner, and it should have a low pour point and low viscosity to maintain fluidity during low temperature operation.

The provided apparatus may include a mechanism for transferring heat. The mechanism may include a heat transfer fluid. The heat transfer fluid may include one or more hydrofluoroolefin compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature-controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal communication with the device. The heat transfer mechanism, when placed in thermal communication with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to a thermal management system for a battery pack (e.g., lithium-ion battery pack). The system may include a battery pack and a working fluid in thermal communication with the battery pack. The working fluid may include one or more hydrofluoroolefins of the present disclosure.

LISTING OF EMBODIMENTS

1. A hydrofluoroolefin compound represented by the following general formula (I):

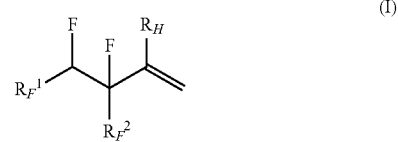

where $R_H$ is a hydrogen atom or $CH_3$; and
(i) $R_F1$ is a linear or branched perfluorinated alkyl group having 1 to 10 carbon atoms and optionally including one or more catenated heteroatoms; and $R_F2$ is a fluorine atom or a linear or branched perfluorinated alkyl group having 1 to 8 carbon atoms and optionally including one or more catenated heteroatoms; with the proviso that when $R_F2$ is a fluorine atom, then $R_F1$ includes at least 2 carbon atoms; or
(ii) $R_F1$ and $R_F2$ are bonded together to form a ring structure having 4 to 8 carbon atoms and optionally including one or more catenated heteroatoms.

2. The hydrofluoroolefin compound of embodiment 1, wherein the hydrofluoroolefin compound has a solubility factor greater than 0.

3. The hydrofluoroolefin compound of any one of the previous embodiments, wherein the hydrofluoroolefin compound is non-flammable according to ASTM D-3278-96 e-1 test method.

4. A working fluid comprising a hydrofluoroolefin according to any one of embodiments 1-3, wherein the hydrofluoolefin is present in the working fluid at an amount of at least 25% by weight based on the total weight of the working fluid.

5. A composition comprising:
   a hydrofluoroolefin compound of any one of embodiments 1-3; and
   a contaminant;
   wherein the hydrofluoolefin is present in the composition at an amount of at least 25% by weight, based on the total weight of the composition.
6. The composition of embodiment 5, wherein the contaminant comprises a long chain hydrocarbon alkane.
7. A cleaning composition comprising:
   a hydrofluoroolefin compound or working fluid according to any one of embodiments 1-4; and
   a co-solvent.
8. The cleaning composition of embodiment 7, wherein said hydrofluoroolefin compound is greater than 50 percent by weight of said cleaning composition, based on the total weights of the hydrofluoroolefin compound and the co-solvent.
9. The composition according to any one of embodiments 7-8, wherein said co-solvent comprises alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.
10. A cleaning composition comprising:
    a hydrofluoroolefin compound according to any one of embodiments 1-3; and
    a surfactant.
11. The composition of embodiment 10, wherein the cleaning composition comprises from 0.1 to 5 percent by weight surfactant, based on the total weights of the hydrofluoroolefin compound and the surfactant.
12. The composition of any one of embodiments 10-11, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.
13. An apparatus for heat transfer comprising:
    a device; and
    a mechanism for transferring heat to or from the device, the mechanism comprising a working fluid that comprises a hydrofluoroolefin compound of any one of embodiments 1-3.
14. The apparatus for heat transfer of embodiment 13, wherein the device is selected from a microprocessor, a semiconductor wafer used to manufacture a semiconductor device, a power control semiconductor, an electrochemical cell, a battery pack, an electrical distribution switch gear, a power transformer, a circuit board, a multi-chip module, a packaged or unpackaged semiconductor device, a fuel cell, and a laser.
15. The apparatus for heat transfer of embodiment 13, wherein the mechanism for transferring heat is a component in a system for maintaining a temperature or temperature range of an electronic device.
16. A method of transferring heat comprising:
    providing a device; and
    transferring heat to or from the device using a heat transfer fluid that comprises a hydrofluoroolefin compound of any one of embodiments 1-3.
17. A thermal management system for a battery pack comprising:
    a battery pack; and
    a working fluid in thermal communication with the battery pack;
    wherein the working fluid comprises a hydrofluoroolefin compound of any one of embodiments 1-3.
18. A process for removing contaminants from a substrate, the process comprising the steps of:
    contacting a substrate with a hydrofluoroolefin compound according to any one of embodiments 1-3;
    wherein the contaminant comprises a long chain hydrocarbon alkane.

EXAMPLES

Objects and advantages of this disclosure are further illustrated by the following illustrative examples. Unless otherwise noted, all parts, percentages, ratios, etc. in the examples and the rest of the specification are by weight, and all reagents used in the examples were obtained, or are available, from general chemical suppliers such as, for example, Sigma-Aldrich Corp., Saint Louis, MO, US or Alfa Aesar, Haverhill, MA, US, or may be synthesized by conventional methods.

The following abbreviations are used herein: mL=milliliters, mol=moles, g=grams, ° C.=degrees Celsius. "Room temperature" refers to an ambient temperature of approximately 20-25° C., with a typical average of 23° C.

TABLE 1

| Materials | | |
| --- | --- | --- |
| Material | Description | Source |
| C-9 hydrocarbon | $C_9H_{20}$, mp = −53.5° C. | Sigma-Aldrich Corp., Saint Louis, MO, US |
| C-10 hydrocarbon | $C_{10}H_{22}$, mp = −29.7° C. | Sigma-Aldrich Corp., Saint Louis, MO, US |
| C-11 hydrocarbon | $C_{11}H_{24}$, mp = −25° C. | Sigma-Aldrich Corp., Saint Louis, MO, US |
| C-12 hydrocarbon | $C_{12}H_{26}$, mp = −9.6° C. | Sigma-Aldrich Corp., Saint Louis, MO, US |
| C-13 hydrocarbon | $C_{13}H_{28}$, mp = −5.4° C. | Sigma-Aldrich Corp., Saint Louis, MO, US |
| C-14 hydrocarbon | $C_{14}H_{30}$, mp = 5.9° C. | Sigma-Aldrich Corp., Saint Louis, MO, US |
| C-15 hydrocarbon | $C_{15}H_{32}$, mp = 9.9° C. | Sigma-Aldrich Corp., Saint Louis, MO, US |
| C-16 hydrocarbon | $C_{16}H_{34}$, mp = 18.2° C. | Sigma-Aldrich Corp., Saint Louis, MO, US |
| C-17 hydrocarbon | $C_{17}H_{36}$, mp = 21° C. | Sigma-Aldrich Corp., Saint Louis, MO, US |
| C-18 hydrocarbon | $C_{18}H_{38}$, mp = 28-30° C. | Sigma-Aldrich Corp., Saint Louis, MO, US |
| C-19 hydrocarbon | $C_{19}H_{40}$, mp = 32-34° C. | Sigma-Aldrich Corp., Saint Louis, MO, US |
| C-20 hydrocarbon | $C_{20}H_{42}$, mp = 36.7° C. | Sigma-Aldrich Corp., Saint Louis, MO, US |
| C-21 hydrocarbon | $C_{21}H_{44}$, mp = 40.5° C. | Sigma-Aldrich Corp., Saint Louis, MO, US |
| C-22 hydrocarbon | $C_{22}H_{46}$, mp = 42° C. | Sigma-Aldrich Corp., Saint Louis, MO, US |
| C-23 hydrocarbon | $C_{23}H_{48}$, mp = 48-50° C. | Sigma-Aldrich Corp., Saint Louis, MO, US |

Test Methods

Largest Soluble Hydrocarbon (LSH): The LSH of each hydrofluoroolefin compound was determined by mixing the compound with hydrocarbons of varying molecular weight ($C_nH_{2n+2}$, where n=9 to 24) in a hydrofluoroolefin:hydrocarbon ratio of about 1:1 to 1:2 by weight at room temperature (25° C.) and at 50° C. The LSH value is reported as the value of n in the formula $C_nH_{2n+2}$ for the longest hydrocarbon which was compatible with the hydrofluoroolefin without exhibiting haze to the naked eye. A larger value of n is interpreted herein to indicate a greater ability of the hydrofluoroolefin to clean hydrocarbons.

Flash Point: Flash point was measured according to the procedures outlined in ASTM D-3278-96 e-1 "Standard Test Methods for Flash Point of Liquids by Small Scale Closed-Cup Apparatus." Materials that demonstrated no flash point were considered to be non-flammable according to the ASTM test method.

Sample Preparation

Example 1: 3,4,5,5,5-pentafluoro-3-(trifluoromethyl)pent-1-ene

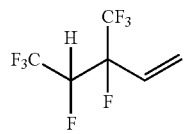

A 600 mL Parr reactor was charged with ethanol (185 g, 4 mol) and t-amyl peroxy-2-ethylhexanoate (22 g, 0.05 mol), then sealed, cooled to −78° C. and evacuated to 10 torr. Perfluoro-2-butene (200 g, 1 mol) was charged from a cylinder and the system was sealed and heated to 70° C. with stirring for 72 hours. The reactor was cooled and the mixture was washed twice with water and once with saturated aqueous sodium bicarbonate. The fluorochemical phase was separated and 244 g of product were collected. The sample was dried over silica gel and used in the next reaction with no further purification.

A 1000 mL round bottom, 3-neck flask was fitted with overhead stirrer, addition funnel, cold water condenser, and thermocouple, then charged with 3,4,5,5,5-pentafluoro-3-(trifluoromethyl)pentan-2-ol (244 g, 0.99 mol) and Montmorillonite K10 (1 g). Acetic anhydride (212 g, 2.08 mol) was added via addition funnel with rapid stirring. After a slight exotherm ceased, the mixture was stirred at 60° C. overnight. The flask was cooled to room temperature and dilute sodium bicarbonate solution was added slowly via the addition funnel. After 1 hour of stirring at room temperature, the mixture was poured into a separatory funnel. The aqueous phase tested acidic and the process was repeated. The fluorocarbon phase was separated, water washed, then dried over sodium sulfate. 218 g of product were obtained.

The acetate was thermally decomposed and the title product separated by fractional distillation. The structure was verified by GC-MS and NMR. A sample was subjected to flashpoint analysis in accordance ASTM method D7236-96 e-1 and no flash point was identified.

Example 2: Preparation of 1,1,2,2,3,3,4,4,5,6-decafluoro-5-isopropenyl-cyclohexane

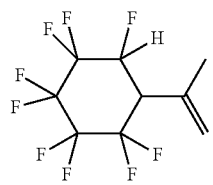 [SMILES: C=C(C)C1C(F)C(F)(F)C(F)(F)C(F)(F)C1(F)F]

A 600 mL Parr reactor was charged with isopropanol (69 g, 1.15 mol), t-amyl peroxy-2-ethylhexanoate (2 g, 0.01 mol), and perfluorocyclohexene (75 g, 0.29 mol) then sealed and heated to 70° C. with vigorous stirring overnight. The reactor was cooled to room temperature and the reactor contents were transferred to a separatory funnel. The fluorochemical phase was washed twice with water then placed in a 100 mL flask fitted with distillation head and magnetic stirrer. The flask contents were distilled until the pot temperature rose to 110° C. 32.6 g of material was collected and used in the next reaction without further purification.

In a manner similar to Example 1, the polyfluorinated alcohol intermediate was acylated and thermally decomposed to produce the title compound. The product was verified by GC-MS.

Example 3: Preparation of 1,1,2,2,3,3,4,4,5,6-decafluoro-5-vinyl-cyclohexane

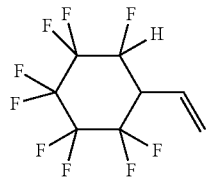

A 600 mL Parr reactor was charged with ethanol (53 g, 1.15 mol), perfluorocyclohexene (75 g, 0.29 mol), and t-amyl peroxy-2-ethylhexanoate (2 g, 0.01 mol), sealed, then heated to 70° C. with vigorous stirring overnight. The reactor was cooled, and the mixture was washed twice with water and once with saturated aqueous sodium bicarbonate. The crude product was dried over silica gel, filtered, then distilled up to a pot temperature of 120° C. The remaining reactor contents were collected and used in the next reaction without further purification.

In a manner similar to Example 1, the polyfluorinated alcohol intermediate was acylated and thermally decomposed to produce the title compound. The product was verified by GC-MS.

Example 4: Preparation of 1,1,2,2,3,3,4-heptafluoro-5-isopropenyl-cyclopentane

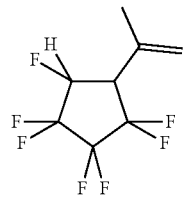

A 600 mL Parr reactor was charged with isopropanol (85 g, 1.4 mol) and t-amyl peroxy-2-ethylhexanoate (3.5 g, 0.02 mol), then sealed, cooled to −78° C. and evacuated to 10 torr. Perfluorocyclopentene (100 g, 0.47 mol) was charged from a cylinder. The system was sealed and heated to 70° C. with vigorous stirring overnight. The reactor was cooled, and the mixture was washed twice with water and once with saturated bicarbonate solution. The product was dried over silica gel and analyzed by GC-FID. The sample was filtered and distilled to a pot temperature of 110° C. The pot contents were collected, and pure product was verified by GC-FID.

In a manner similar to Example 1, the polyfluorinated alcohol intermediate was acylated and thermally decomposed to produce the title compound. The structure was verified by GC-MS and NMR.

Example 5: Preparation of 1,1,2,2,3,3,4-heptafluoro-5-vinyl-cyclopentane

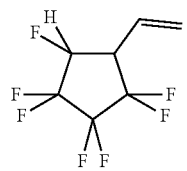

A 600 mL Parr reactor was charged with ethanol (85 g, 1.85 mol) and t-amyl peroxy-2-ethylhexanoate (3.5 g, 0.02 mol), then sealed, cooled to −78° C., and evacuated to 10 torr. Perfluorocyclopentene (100 g, 0.47 mol) was charged from a cylinder. The system was sealed and heated to 70° C. with vigorous stirring overnight. The reactor was cooled and the mixture was washed twice with water and once with saturated bicarbonate solution. Unreacted F-cyclopentene and ethanol were distilled off until the pot temperature rose above 100° C. The pot contents were collected, giving 123.7 g of pure product.

In a manner similar to Example 1, the polyfluorinated alcohol intermediate was acylated and thermally decomposed to produce the title compound. The product was verified by GC-MS.

Example 6: Preparation of 3,4,5,6,6,6-hexafluoro-3,5-bis(trifluoromethyl)hex-1-ene

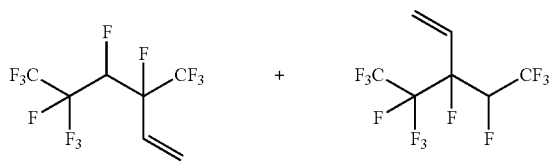

In a manner similar to the Examples 1-5, perfluoro-4-methyl-2-pentene was reacted with ethanol to give a polyfluorinated alcohol intermediate. This intermediate was acylated and thermally decomposed to produce the title compound. The product was verified by GC-MS.

Results

Table 2 summarizes results of Largest Soluble Hydrocarbon (LSH) testing of Examples 1 and 4. The results presented in Table 2 indicate that the hydrofluoroolefins of the present invention are highly suitable fluids for cleaning applications.

TABLE 2

| | Largest Soluble Hydrogen | |
| --- | --- | --- |
| | LSH (n in $C_nH_{2n+2}$) | |
| Example | 25° C. | 50° C. |
| 1 | 13 | 14 |
| 4 | 17 | 21 |

Example 1 exhibited no flash point. Example 4 was not observed to burn in an open pan upon exposure to direct flame.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:

1. A hydrofluoroolefin compound represented by the following general formula (I):

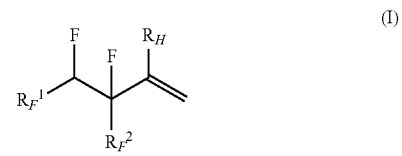

where $R_H$ is a hydrogen atom or $CH_3$; and
   (i) $R_F1$ is a linear or branched perfluorinated alkyl group having 1 to 10 carbon atoms and optionally including one or more catenated heteroatoms; and $R_F2$ is a linear or branched perfluorinated alkyl group having 1 to 8 carbon atoms and optionally including one or more catenated heteroatoms; or
   (ii) $R_F1$ and $R_F2$ are bonded together to form a ring structure having 5 to 6 carbon atoms and optionally including one or more catenated heteroatoms.

2. The hydrofluoroolefin compound of claim 1, wherein the hydrofluoroolefin compound has a solubility factor greater than 0.

3. The hydrofluoroolefin compound of claim 1, wherein the hydrofluoroolefin compound is non-flammable according to ASTM D-3278-96 e-1 test method.

4. A working fluid comprising a hydrofluoroolefin according to claim 1, wherein the hydrofluoolefin is present in the working fluid at an amount of at least 25% by weight based on the total weight of the working fluid.

5. A composition comprising:
   a hydrofluoroolefin compound of claim 1; and
   a contaminant;
   wherein the hydrofluoolefin is present in the composition at an amount of at least 25% by weight, based on the total weight of the composition.

6. The composition of claim 5, wherein the contaminant comprises a long chain hydrocarbon alkane.

7. A cleaning composition comprising:
a hydrofluoroolefin compound or working fluid according to claim 1; and
a co-solvent.

8. The cleaning composition of claim 7, wherein said hydrofluoroolefin compound is greater than 50 percent by weight of said cleaning composition, based on the total weights of the hydrofluoroolefin compound and the co-solvent.

9. The composition according claim 7, wherein said co-solvent comprises alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.

10. A cleaning composition comprising:
a hydrofluoroolefin compound according to claim 1; and
a surfactant.

11. The composition of claim 10, wherein the cleaning composition comprises from 0.1 to 5 percent by weight surfactant, based on the total weights of the hydrofluoroolefin compound and the surfactant.

12. The composition of claim 10, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.

13. An apparatus for heat transfer comprising:
a device; and
a mechanism for transferring heat to or from the device, the mechanism comprising a working fluid that comprises a hydrofluoroolefin compound of claim 1.

14. The apparatus for heat transfer of claim 13, wherein the device is selected from a microprocessor, a semiconductor wafer used to manufacture a semiconductor device, a power control semiconductor, an electrochemical cell, a battery pack, an electrical distribution switch gear, a power transformer, a circuit board, a multi-chip module, a packaged or unpackaged semiconductor device, a fuel cell, and a laser.

15. The apparatus for heat transfer of claim 13, wherein the mechanism for transferring heat is a component in a system for maintaining a temperature or temperature range of an electronic device.

16. A method of transferring heat comprising:
providing a device; and
transferring heat to or from the device using a heat transfer fluid that comprises a hydrofluoroolefin compound of claim 1.

17. A thermal management system for a battery pack comprising:
a battery pack; and
a working fluid in thermal communication with the battery pack;
wherein the working fluid comprises a hydrofluoroolefin compound of claim 1.

18. A process for removing contaminants from a substrate, the process comprising the steps of:
contacting a substrate with a hydrofluoroolefin compound according to claim 1;
wherein the contaminant comprises a long chain hydrocarbon alkane.

* * * * *